United States Patent [19]
Frank et al.

[11] Patent Number: 6,111,088
[45] Date of Patent: Aug. 29, 2000

[54] NUCLEOTIDE SEQUENCE ENCODING A 52 KDA RO/SSA AUTOANTIGEN

[75] Inventors: Mark Barton Frank, Edmond; Kazuko Itoh, Oklahoma City, both of Okla.

[73] Assignee: Oklahoma Medical Research Foundation, Oklahoma City, Okla.

[21] Appl. No.: 07/945,830

[22] Filed: Sep. 16, 1992

Related U.S. Application Data

[63] Continuation of application No. 07/520,270, May 7, 1990, abandoned.

[51] Int. Cl.[7] .............................. C07H 21/04; C12Q 1/68; C12N 1/08; C08G 63/82
[52] U.S. Cl. .................... 536/23.5; 536/24.1; 536/24.31; 435/6; 435/270; 435/252.3; 435/320.1; 530/358; 530/389.2
[58] Field of Search ................................ 536/23.5, 24.1, 536/24.31; 435/6, 270, 252.3, 320.1; 530/358, 389.2

[56] References Cited

U.S. PATENT DOCUMENTS 4,711,955  12/1987  Ward et al. ................................ 536/29

OTHER PUBLICATIONS

R. M. Bernstein, et al., *Mol. Biol. Med.* 2:105–120 (1984).
J. B. Harley and K. K. Gaither, Autoantibodies In Rheumatic Disease Clinics of North America: Systemic Lupus Erythematosus 14:1, 43–56 (1988).
K. K. Gaither, et al. *J. Clin. Invest.* 79:841–846 (1987).
T, J. A. Lehman, et al., *J. Rheumatol.* 11;644–647 (1984).
M. Calmes and B. A. Bartholomew, *J. Clin. Pathol.* 38:73–75 (1985).
P. J. Maddison, et al., *J. Rheumatol.* 5:407–411 (1978).
K. K. Gaither and J. B. Harley, *Prot. Biol. Fluids Proc. Colloq.* 33,413–416 (1985).
J. B. Harley, et al., *Arthritis Rheum.* 29:196–206 (1986).
Ben–Chetrit, et al., *J. Exp. Med.* 167, 1560–1571 (1988).
M. D. Rader, et al., *J. Clin. Invest.* 83:1293–1298 (1989).

*Primary Examiner*—Kenneth R. Horlick
*Assistant Examiner*—Jeffrey Siew
*Attorney, Agent, or Firm*—Arnall Golden & Gregory, LLP

[57] ABSTRACT

Complementary DNA encoding a 52 kDa form of a protein present in the human Ro/SSA ribonucleoprotein complex has been cloned. A lambda gt11 cDNA library made from human thymocyte mRNA was screened with serum from a SLE patient and two immunoreactive clones were isolated. These clones reacted with other patient sera which had anti-52 kDa Ro/SSA antibodies and with affinity purified anti-52 kDa Ro/SSA antibodies. Moreover, affinity purified antibodies eluted from fusion proteins of the isolated clones reacted only with the 52 kDa protein of lymphocytes in the Western blot. Ro/SSA RNAs were also precipitated with these affinity purified antibodies, further confirming that the clones encode a 52 kDa Ro/SSA antigen. The sequence differs from the previously reported 60 kDa Ro/SSA gene.

7 Claims, 6 Drawing Sheets

```
         10         20         30
GAATTCGGGC ACACTGCTGT TTAACGGCAC
         40         50         60
ACTTGACAAT GGCTTCAGCA GCACGCTTGA
         70         80         90
CAATGATGTG GGAGGAGGTC ACATGCCCTA
        100        110        120
TCTGCCTGGA CCCCTTCGTG GAGCCTGTGA
        130        140        150
GCATCGAGTG TGGCCACAGC TTCTGCCAGG
        160        170        180
AATGCATCTC TCAGGTTGGG AAAGGTGGGG
        190        200        210
GCAGCGTCTG TCCTGTGTGC CGGCAGCGCT
        220        230        240
TTCTGCTCAA GAATCTCCGG CCCAATCGAC
        250        260        270
AGCTAGCCAA CATGGTGAAC AACCTTAAAG
        280        290        300
AAATCAGCCA GGAGGCCAGA GAGGGCACAC
        310        320        330
AGGGGGAACG GTGTGCAGTG CATGGAGAGA
        340        350        360
GACTTCACCT GTTCTGTGAG AAAGATGGGA
        370        380        390
AGGCCCTTTG CTGGGTATGT GCCCAGTCTC
        400        410        420
GGAAACACCG TGACCACGCC ATGGTCCCTC
        430        440        450
TTGAGGAGGC TGCACAGGAG TACCAGGAGA
        460        470        480
AGCTCCAGGT GGCATTAGGG GAACTGAGAA
```

```
            10         20         30
        GAATTCGGGC ACACTGCTGT TTAACGGCAC
            40         50         60
        ACTTGACAAT GGCTTCAGCA GCACGCTTGA
            70         80         90
        CAATGATGTG GGAGGAGGTC ACATGCCCTA
           100        110        120
        TCTGCCTGGA CCCCTTCGTG GAGCCTGTGA
           130        140        150
        GCATCGAGTG TGGCCACAGC TTCTGCCAGG
           160        170        180
        AATGCATCTC TCAGGTTGGG AAAGGTGGGG
           190        200        210
        GCAGCGTCTG TCCTGTGTGC CGGCAGCGCT
           220        230        240
        TTCTGCTCAA GAATCTCCGG CCCAATCGAC
           250        260        270
        AGCTAGCCAA CATGGTGAAC AACCTTAAAG
           280        290        300
        AAATCAGCCA GGAGGCCAGA GAGGGCACAC
           310        320        330
        AGGGGGAACG GTGTGCAGTG CATGGAGAGA
           340        350        360
        GACTTCACCT GTTCTGTGAG AAAGATGGGA
           370        380        390
        AGGCCCTTTG CTGGGTATGT GCCCAGTCTC
           400        410        420
        GGAAACACCG TGACCACGCC ATGGTCCCTC
           430        440        450
        TTGAGGAGGC TGCACAGGAG TACCAGGAGA
           460        470        480
        AGCTCCAGGT GGCATTAGGG GAACTGAGAA
```

FIG. 1A

```
          490        500        510
     GAAAGCAGGA GTTGGCTGAG AAGTTGGAAG
          520        530        540
     TGGAAATTGC AATAAAGAGA GCAGACTGGA
          550        560        570
     AGAAAACAGT GGAAACACAG AAATCTAGGA
          580        590        600
     TTCACGCAGA GTTTGTGCAG CAAAAAACT
          610        620        630
     TCCTGGTTGA AGAAGAACAG AGGCAGCTGC
          640        650        660
     AGGAGCTGGA GAAGGATGAG AGGGAGCAGC
          670        680        690
     TGAGAATCCT GGGGGAGAAA GAGGCCAAGC
          700        710        720
     TGGCCCAGCA GAGCCAGGCC CTACAGGAGC
          730        740        750
     TCATCTCAGA GCTAGATCGA AGGTGCCACA
          760        770        780
     GCTCAGCACT GGAACTGCTG CAGGAGGTGA
          790        800        810
     TAATTGTCCT GGAAGGAGT GAGTCCTGGA
          820        830        840
     ACCTGAAGGA CCTGGATATT ACCTCTCCAG
          850        860        870
     AACTCAGGAG TGTGTGCCAT GTGCCAGGGC
          880        890        900
     TGAAGAAGAT GCTGAGGACA TGTGCAGTCC
          910        920        930
     ACATCACTCT GGATCCAGAC ACAGCCAATC
          940        950        960
     CGTGGCTGAT ACTTTCAGAA GATCGGAGAC
```

FIG. 1B

|  970 | 980 | 990 |
|---|---|---|
| AAGTGAGGCT | TGGAGACACC | CAGCAGAGCA |
| 1,000 | 1,010 | 1,020 |
| TACCTGGAAA | TGAAGAGAGA | TTTGATAGTT |
| 1,030 | 1,040 | 1,050 |
| ATCCTATGGT | CCTGGGTGCC | CAGCACTTTC |
| 1,060 | 1,070 | 1,080 |
| ACTCTGGAAA | ACATTACTGG | GAGGTAGATG |
| 1,090 | 1,100 | 1,110 |
| TGACAGGAAA | GGAGGCCTGG | GACCTGGGTG |
| 1,120 | 1,130 | 1,140 |
| TCTGCAGAGA | CTCTGTGCGC | AGGAAGGGGC |
| 1,150 | 1,160 | 1,170 |
| ACTTTTTGCT | TAGTTCCAAG | AGTGGCTTCT |
| 1,180 | 1,190 | 1,200 |
| GGACAATTTG | GTTGTGGAAC | AAACAAAAAT |
| 1,210 | 1,220 | 1,230 |
| ATGAGGCTGG | CACCTACCCC | CAGACTCCCC |
| 1,240 | 1,250 | 1,260 |
| TCCACCTTCA | GGTGCCTCCA | TGCCAAGTTG |
| 1,270 | 1,280 | 1,290 |
| GGATTTTCCT | GGACTATGAG | GCTGGCATGG |
| 1,300 | 1,310 | 1,320 |
| TCTCCTTCTA | CAACATCACT | GACCATGGCT |
| 1,330 | 1,340 | 1,350 |
| CCCTCATCTA | CTCCTTCTCT | GAATGTGCCT |
| 1,360 | 1,370 | 1,380 |
| TTACAGGACC | TCTGCGGCCC | TTCTTCAGTC |
| 1,390 | 1,400 | 1,410 |
| CTGGTTTCAA | TGATGGAGGA | AAAAACACAG |
| 1,420 | 1,430 | 1,440 |
| CCCCTCTAAC | CCTCTGTCCA | CTGAATATTG |

FIG. 1C

```
        1,450        1,460        1,470
   GATCACAAGG   ATCCACTGAC   TATTGATGGC
        1,480        1,490        1,500
   TTTCTCTGGA   CACTGCCACT   CTCCCCATTG
        1,510        1,520        1,530
   GCACCGCTTC   TCAGCCACAA   ACCCTGCCTC
        1,540        1,550        1,560
   TTTTCCCCAT   GAACTCTGAA   CCACCTTTGT
        1,570        1,580        1,590
   CTCTGCAGAG   GCATCCGGAT   CCCAGCAAGC
        1,600        1,610        1,620
   GAGCTTTAGC   AGGGAAGTCA   CTTCACCATC
        1,630        1,640        1,650
   AACATTCCTG   CCCCAGATGG   CTTTGTGATT
        1,660        1,670        1,680
   CCCTCCAGTG   AAGCAGCCTC   CTTATATTTG
        1,690        1,700        1,710
   GCCCAAACTC   ATCTTGATCA   ACCAAAAACA
        1,720        1,730        1,740
   TGTTTCTGCC   TTCTTTATGG   GACTTAAGTT
        1,750        1,760        1,770
   TTTTTTTTCT   CCTCTCCATC   TCTAGGATGT
        1,780        1,790        1,800
   CGTCTTTGGT   GAGATCTCTA   TTATATCTTG
        1,810        1,820        1,830
   TATGGTTTGC   AAAAGGGCTT   CCTAAAAATA
        1,840        1,850
   AAAACCCGAA   TTC
```

NUCLEOTIDE SEQUENCE ENCODING A 52 KDA RO/SSA AUTOANTIGEN

This is a continuation of application Ser. No. 07/520,270 filed on May 7, 1990 now abandoned.

BACKGROUND OF THE INVENTION

The present invention is the nucleotide sequence encoding a 52 kDa Ro/SSA autoantigen found in some systemic lupus erythematosus and Sjogren's syndrome patients, the encoded protein and methods for use thereof in diagnostic and therapeutic applications.

Systemic lupus erythematosus (SLE) is similar to many other disorders in which autoantibodies are found and thought to be important in etiology and pathogenesis. SLE can be grouped with those diseases that commonly have autoantibodies present but for whom a central role of autoantibody in pathogenesis leading to clinical expression has yet to be fully established or accepted. Other such diseases include Sjogren's syndrome, rheumatoid arthritis, insulin-dependent diabetes mellitus, primary biliary cirrhosis, Wegener's granulomatosis, inflammatory bowel disease, polymyositis, dermatomyositis, scleroderma, and many others.

Typically, autoimmune diseases present with a wide array of symptoms and clinical signs. The production of circulating autoantibodies to ribonucleoprotein complexes (RNPs) is a unifying characteristic of some of the rheumatic autoimmune diseases. The most common antigens in SLE and closely related disorders include: Ro/SSA, La/SSB, nRNP and Sm. Initially, these antibodies were found using double immunodiffusion, but more recently sensitive solid phase assays have been developed to quantitate the autoantibodies. The Ro/SSA RNA-protein particle has been found to be a constituent of all human cells evaluated to date. Approximately half of Sjogren's syndrome and systemic lupus erythematosus (lupus) patients have anti-Ro/SSA precipitins. Approximately 75% of patients with subacute cutaneous lupus erythematosus or complement component C2 deficiency with SLE have anti-Ro/SSA precipitins, and virtually all patients with C2 or C4 deficiency have elevated levels of anti-Ro/SSA when measured by ELISA. Over 80% of mothers of newborns with neonatal lupus dermatitis or complete congenital heart block have these autoantibodies. As many as 5% of patients with rheumatoid arthritis, polymyositis, and progressive systemic sclerosis have anti-Ro/SSA, as reported by R. M. Bernstein, et al., *Mol. Biol. Med.* 2:105–120 (1984); and J. B. Harley and K. K. Gaither, *Autoantibodies. In Rheumatic Disease Clinics of North American: Systemic Lupus Erythematosus* 14:1, 43–56 (1988).

It has also been shown that some normal individuals have low levels of anti-Ro/SSA, that some normal family members of SLE patients have anti-Ro/SSA, and that 1% of normal pregnant women, and 0.1% of a cohort of hospitalized patients have precipitating levels of this autoantibody (K. K. Gaither, et al., *J. Clin. Invest.* 79:841–846 (1987); T. J. A. Lehman, et al., *J. Rheumatol.* 11:644–647 (1987); M. Calmes and B. A. Bartholomew, *J. Clin. Pathol.* 38:73–75 (1985); P. J. Maddison, et al., *J. Rheumatol.* 5:407–411 (1978)). Even if the anti-Ro/SSA autoantibody is not pathogenic, the concentrations of anti-Ro/SSA autoantibody achieved by patients can be extraordinary, and is commonly higher than 1 mg/ml of specific anti-Ro/SSA immunoglobulin (K. K. Gaither and J. B. Harley, *Prot. Biol. Fluids Proc. Collog.* 33:413–416 (1985); J. B. Harley, et al., *Arthritis Rhuem.* 29:196–206 (1986)). The immune system derangement leading to this specific overproduction of anti-Ro/SSA is not apparent but is likely to reflect a fundamental mechanism related to the immunopathogenesis of the related diseases.

Ro/SSA has been referred to by several other names, including "SSA/Ro", "SS-A/Ro", "SS-A", "Ro", and "Ro (SSA)". Historically, the biochemical characterization of the Ro/SSA complex has centered around a 60 kDa protein associated with one of four hY RNAs, ranging from 80 to 112 bases, although the antigenic reactivity of the complex appears to be independent of the RNA. The Ro/SSA family of proteins has now been shown to have several molecular forms which are operationally defined by the molecular weight of the antigen identified. As reviewed by Ben-Chetrit, et al., in *J. Exp. Med.* 167, 1560–1571 (1988), the protein components of Ro/SSA have been described as polypeptides having molecular masses ranging from 50 to 150 kiloDaltons (kD). A major form has an apparent molecular weight of 60 kDa. Recently, two additional proteins bound by anti-Ro/SSA sera have been identified by M. D. Rader, et al., *J. Clin. Invest.* 83:1556–1562 (1989), with molecular weights of 52 kDa and 54 kDa. Ben-Chetrit, et al., (1988) also report a 52 kDa protein. Chan, et al., reported at the Molecular and Cell Biology of Autoantibodies and Autoimmunity, First International Workshop, Jul. 27–29 (1989), that they had cloned a gene encoding a 46 kDa protein reactive with antisera against a 52 kDa Ro/SSA protein that was distinct, based on sequence comparison, from the cDNA of 60 kDa Ro/SSA. Other groups have confidentially reported that they have isolated cDNA encoding a different 60 kDa protein, having a molecular weight predicted by sequence analysis of 48 kDa.

It is impossible to determine at this time how many different autoantigens are produced which form complexes with RNA and that are characteristic, or involved in the pathogenesis, of autoimmune disorders in humans, such as SLE and Sjogren's syndrome. The proteins may vary not only from patient to patient, but in cellular origin. For example, in nucleated cells, 60, 52 and perhaps 45 kDa forms of the Ro/SSA protein have been found using Western blot analysis. Certain lupus patient sera contain antibodies which recognize only the 60 kDa form, others only the 52 kDa form, and others have antibodies which bind to both the 60 and 52 kDa forms. In red blood cells, 60 and 54 kDa proteins have been identified in Ro/SSA particles. It appears that these proteins can only be identified with any certainty by comparison of nucleotide and amino acid sequence comparison.

It is therefore an object of the present invention to provide cDNA encoding an autoantigen characterized by a molecular weight of approximately 52 kDa to which serum antibodies are produced by certain patients having autoimmune disorders.

It is a further object of the present invention to provide the cDNA and the protein encoded by the cDNA and methods for use thereof for diagnostic and therapeutic purposes.

SUMMARY OF THE INVENTION

Complementary DNA encoding a 52 kDa form of a protein present in the human Ro/SSA ribonucleoprotein complex has been cloned. A lambda gt11 cDNA library made from human thymocyte mRNA was screened with serum from a SLE patient and two immunoreactive clones were isolated. These clones reacted with other patient sera which had anti-52 kDa Ro/SSA antibodies and with affinity purified anti-52 kDa Ro/SSA antibodies. Moreover, affinity purified antibodies eluted from fusion proteins of the isolated clones reacted only with the 52 kDa protein of lymphocytes in the Western blot. Ro/SSA RNAs were also precipitated with these affinity purified antibodies, further confirming that the clones encode a 52 kDa Ro/SSA antigen. The sequence differs from the previously reported 60 kDa Ro/SSA gene.

Both the cDNA and the protein expressed therefrom, or portions of either, are useful as diagnostic and therapeutic agents in the identification and treatment of patients having autoantibodies and in the identification and analysis of the structural and functional properties of autoantigens reactive with antibodies to the 52 kDa protein. The cDNA is also useful in the isolation of nucleic acids encoding related proteins. The related proteins can be expressed from these sequences and are also useful as diagnostic and therapeutic agents.

BRIEF DESCRIPTION OF THE DRAWING

FIGS. 1A–1D show the cDNA sequence for the Ro/SSA 52 kDa protein.

FIGS. 2A–2B show the predicted amino acid sequence of this gene. The predicted size of the polypeptide encoded by this sequence is 54,108 daltons.

Figure 2A:
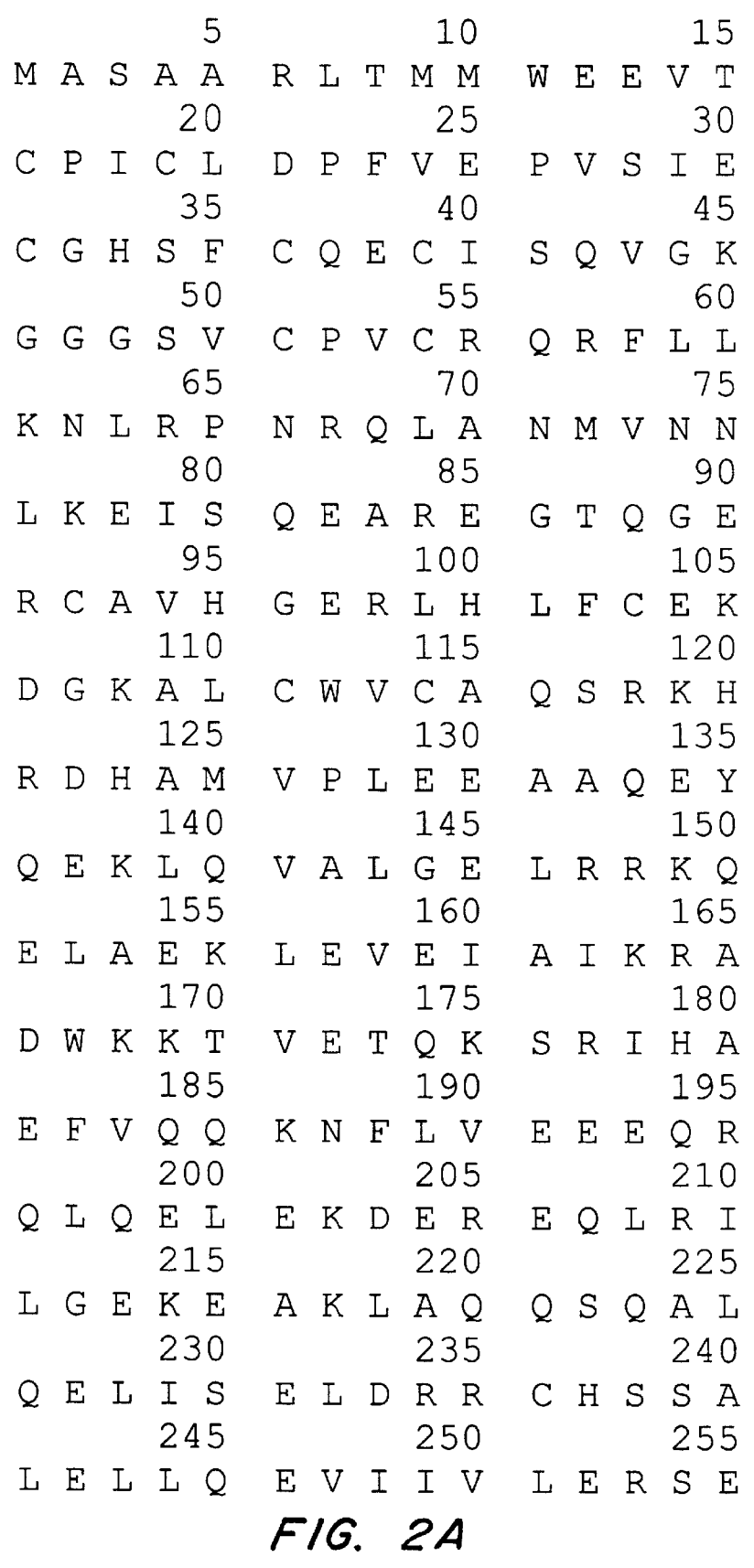
Figure 2B:
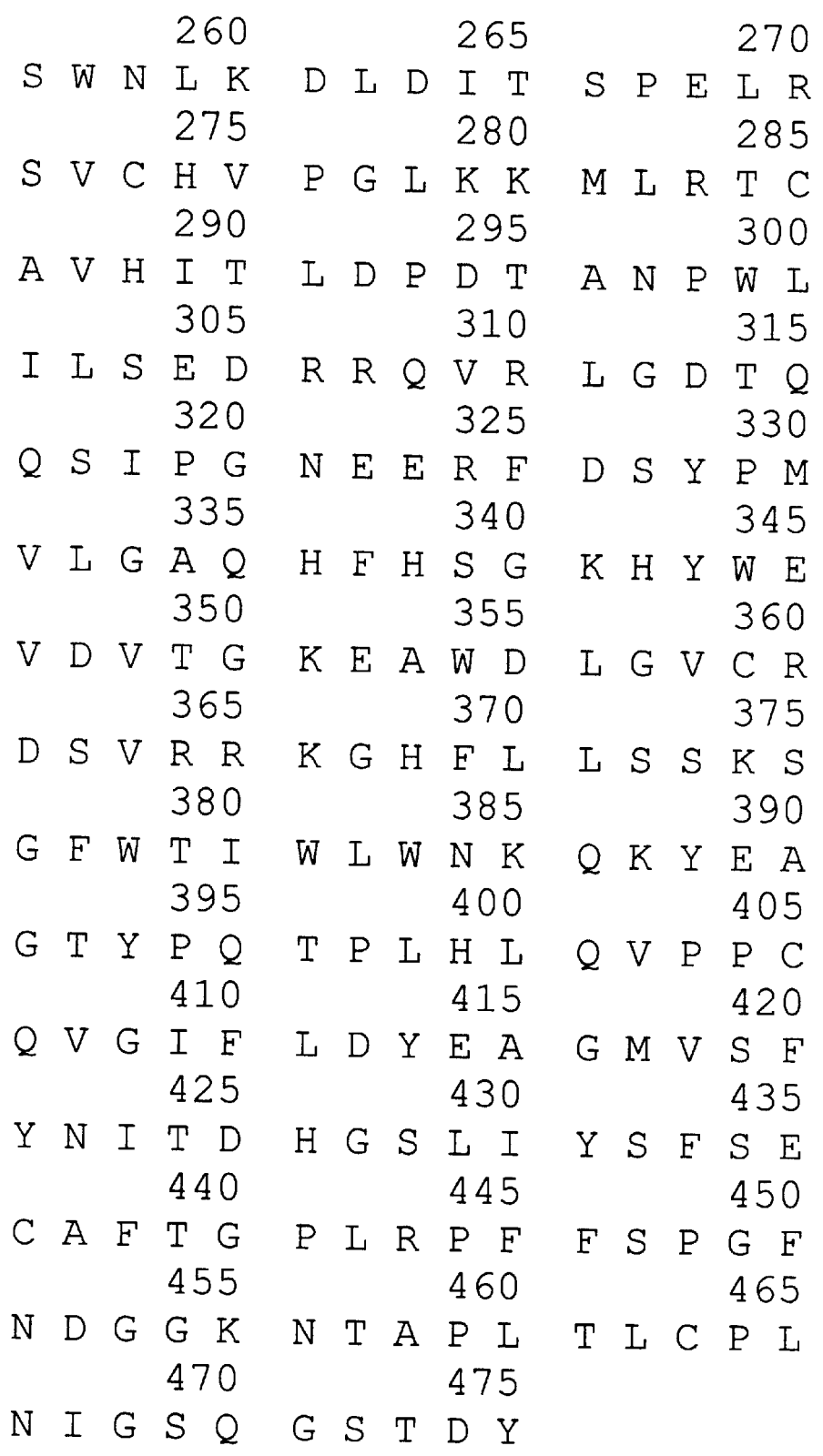

DETAILED DESCRIPTION OF THE INVENTION cDNA encoding a protein having a molecular weight of 52 kDa based on SDS-PAGE and immunological identification in Western blots and a predicted molecular weight of 54,108 daltons has been cloned. The cDNA sequence is shown in FIGS. 1A–1D and the encoded amino acid sequence is shown in FIGS. 2A–2B. The sequence is distinct from any published sequence, including that for two different sequences which may encode the 60 kDa Ro/SSA protein, providing further support for the heterogeneity of this group of proteins. There is similarity between the amino-terminal portions of this predicted protein and the amino-termini of both the mouse rpt-1 protein, a T cell regulatory protein, and the predicted human ret/rfp protein. The level of identity between the amino terminal portion of this cloned protein and the latter two sequences are 48 and 43%, respectively. This area in the three proteins include zinc finger motifs. Further similarity is found between the carboxy-terminal ends of the predicted protein for this 52 kDa Ro/SSA molecule and the human rfp protein (51% identity), suggesting that the gene encoding this Ro/SSA protein may be a member of a larger gene family. It is also possible that polymorphisms of this gene will be identified, i.e. genetic differences in the nucleotide sequence of this gene may exist in humans, perhaps between patients and healthy controls, or in a subset of patients. These polymorphic genes and their protein products (and any of their modified forms) can be identified and isolated using either the disclosed cDNA sequence or protein expressed from the sequence, using techniques known to those skilled in the art, such as those described by Maniatis, et al., *Molecular Cloning. A Laboratory Manual* (Cold Spring Harbor Laboratory, NY 1982). For example, the related sequences can be identified and isolated by hybridization under standard conditions to a probe having a sequence shown in FIGS. 1A–1D (65° C. in the absence of formamide, with unbound probe removed by washing with decreasing concentrations of from 2× to 1×SSPE to 0.5×SSPE).

Referring to FIGS. 1A–1D, the first methionine residue is encoded by an ATG codon beginning at position 39. A stop codon (TGA) is found at position 1464. A putative polyadenylation recognition site (AATAAA) is located at position 1827. This normally occurs approximately 20 bases upstream of poly-A sequences on eukaryotic mRNAs. Thus a 414 base 3' untranslated region occurs on this molecule. The enzyme EcoRI, which has a recognition sequence GAATTC occurring at the beginning and end of this sequence, cleaves this cDNA just short of the poly-A sequence.

As shown in FIGS. 2A–2B, the predicted molecular weight of the encoded protein is slightly larger than the experimentally determined size of the 52 kilodalton protein. Post-translational processing or unusual secondary structure of this gene product is hypothesized to result in the 52 kDa band detected on Western blots.

Protein can be expressed from the cDNA using standard techniques for expression in vitro in cell free translation systems, in bacteria, yeast, and animal cells, including insect, amphibian, avian, and mammalian cells, as well as genetically engineered animals. The techniques are known to those skilled in the art. Reagents, including expression vectors and cell lines, for use in these methods are commercially available.

It is understood that specific cDNA sequences can be modified by those skilled in the art, for example, by labelling, fusion with regulatory sequences, insertion into expression vectors, site-directed mutagenesis and substitution or deletion of nucleotides encoding specific amino acids, without departing from the scope of the nucleotide and amino acid sequences of the present invention, and the methods for their use.

There are several embodiments of diagnostic reagents using the cDNA and protein expressed therefrom, in whole or in part, that can be used for diagnosis of autoimmune disorders or presence of autoantibodies. Antibodies to the protein obtained either from patients, immunized animals, or from antigen-specific monoclonal cell lines can be used to detect the respective antigen in cell extracts or serum and body fluids. These antibody assays include assays such as sandwich ELISA assays, Western immunoblot, radioimmunoassays, and immunodiffusion assays. Techniques for preparing these reagents and methods for use thereof are known to those skilled in the art.

Expressed protein can also be used to immunize animals to generate polyclonal antisera and/or monoclonal antibodies. These, as well as patient autoantibodies, can be used to analyze structure and function of this protein. Protease cleaved fragments of the expressed proteins, or synthetically produced oligopeptides generated from the predicted sequence can be isolated and used to detect autoantibodies, as well as determine the epitope structure of the autoantigens. The expressed protein, or modifications thereof as described above, can be used to purify antibodies from different patients in order to study the heterogeneity of this autoimmune response, and if such heterogeneity is found, to appreciate the relationship between such heterogeneity and disease differences in these patients.

Nucleotide or amino acid probes can be prepared based on the sequence in FIGS. 1A–1D. These are labelled using dyes, or enzymatic, fluorescent, chemiluminescent, or radioactive labels which are commercially available. These probes can be used to detect the expression of this gene or related sequences in cells, tissue samples, or in in vitro reagents, as well as to screen sera or tissue samples from humans suspected of having autoantibody. For example, the appropriate nucleic acid sequences (or their complementary nucleic acid) could be used for in situ hybridization as a method to detect expression of genes encoding the antigen for the autoantibodies in specific tissues or peripheral blood cells. Levels of gene expression can be quantitated in patients and compared to healthy controls, or can be compared between different tissues. Differential tissue expression, coupled with data on tissue pathology and detection of anti-52 kDa antibodies in these tissues, may be used to analyze the relation between antibody binding in vivo and disease pathogenesis. Nucleic acid primers could also be prepared which, with reverse transcriptase or DNA polymerase and the polymerase chain reaction, could be used to expand prospective antigenic sequences. Polymorphisms of this gene may be detected following restriction enzyme digestion of cellular DNA with subsequent electrophoresis and transfer of DNA to a membrane. Products of alleles to the sequence reported in FIGS. 1A–1D may bind to patient autoantibodies with different affinities or may cross-react with epitopes present on other particles. The cDNA probe can also be used to clone the 52 kDa Ro/SSA gene from chromosomal DNA from which questions regarding differential splicing of exons and gene regulation can be addressed. Alterations of the DNA by site-directed mutagenesis may be used to determine functional regions including those which bind to hY RNAs.

Therapeutic applications of the cDNA and proteins expressed therefrom include using the expressed protein to adsorb circulating patient autoantibodies. These proteins, fragments of protein, or oligopeptides derived from the predicted sequence can be bound to solid phase particles over which the patient plasma may pass during plasmapheresis and extracorporeal immunoadsorption, thus reducing anti-Ro/SSA antibody levels before the remaining plasma is returned to the patient. If public idiotypes are found on anti-52 kDa Ro/SSA autoantibodies from different patients, appropriate fragments of these antibodies can be used to generate anti-idiotypic antibodies. The latter antibodies may be used either to block binding of anti-52 kDa antibodies to the native Ro/SSA particle in vivo, or to replace the anti-Ro/SSA molecules discussed above for treatment involving plasmapheresis and extracorporeal immunoadsorption.

The present invention will be further described with reference to the following description of the isolation and characterization of the 52 kDa Ro/SSA protein cDNA.

Absorption of E. coli Antibodies:

Human sera from patients and controls were adsorbed against E. coli following lysis with the bacteriophage vector lambda gt11 to deplete naturally occurring anti-E. coli antibodies from the sera. Briefly, five petri dishes with 30–50,000 plaque forming units (pfu) were plated with E. coli strain Y1090 cells on LB agar and grown for 4 hours at 42° C. Each dish was overlaid with a single nitrocellulose filter for 3 hours on one side and 2 hours on the other side at 37° C. Filters were removed and washed in TBST (50 mM Tris-HCl, pH 8.0; 150 mM NaCl; and 0.5% Tween™-20 (Polyoxyethylene sorbitanmonolaurate, a surfactant)). Filters were then sequentially incubated for one hour each at room temperature with human serum diluted 1:100 in TBST containing 3% bovine serum albumin and 0.02% sodium azide. The success of these adsorptions was monitored by removing a small piece of each filter following the serum incubation, blocking with 5% nonfat dry milk in TBST, washing, and incubating with an alkaline phosphatase conjugated, goat anti-human IgG antisera (Sigma Chemical Co., St. Louis; 1:1000 dilution in TBST containing 5% nonfat dry milk). These filter pieces were then reacted with nitro blue tetrazolium (NBT) and 5-bromo-4-chloro-3-indolylphosphate (BCIP) in alkaline phosphatase buffer (100 mM Tris-HCl, pH 9.5; 100 mM NaCl; 5 mM $MgCl_2$) according to the ProtoBlot System (Promega Corp., Madison).

Screening a Human cDNA Library:

A human thymocyte cDNA library was purchased from Clonetech Laboratories (Palo Alto, Calif.). 30,000 pfus per petri dish were plated with E. coli Y1090 cells on LB agar and incubated at 42° C. for 4 hours. The partially lysed E. coli lawn was then overlaid for 3 hours at 37° C. with a nitrocellulose membrane which had previously been soaked in 10 mM isopropylthio-β-galactoside (IPTG). Filters were removed, washed in TBST, incubated with an E. coli adsorbed patient serum containing antibodies to the 52 kDa Ro/SSA protein, and screened using the alkaline phosphatase method described above. Blue colored positive plaques were plaque purified using the same patient serum. Two clones, FI18.1 and FI19.3, were retested and found to react with sera from a panel of lupus patients which contained autoantibodies which react with the 52 kDa Ro/SSA protein as detected by Western blot assay. IPTG-induced proteins from these clones do not react with antibodies in sera from healthy controls nor patients with autoantibodies to the 60 kDa but not the 52 kDa Ro/SSA polypeptide.

Affinity Purification of Patient Antibodies:

Antibodies were affinity purified from two sources: (1) Western blotted polyacrylamide gels of human lymphocyte or HeLa cell extracts, and (2) nitrocellulose blots of IPTG-induced proteins from the plaque purified clones FI18.1 and FI19.3. For the first method, human cells were lysed by sonication in water and centrifuged to remove debris. Supernatants were reduced, heat denatured, and subjected to electrophoresis on a 10% polyacrylamide gel. Proteins were electrophoretically transferred to nitrocellulose membranes using the method of Towbin, H. T. Staehelin, and J. Gordon *Proc. Natl. Acad. Sci. USA* 76:4350–4354 (1979), from which a small strip was removed, soaked in TBST containing 5% nonfat dry milk, and allowed to react with serum from a patient containing anti-52 kDa Ro/SSA autoantibodies. The filter piece was treated with alkaline phosphatase conjugated anti-human antisera and developed with NBT and BCIP as described above to localize the section of the membrane which contained the Ro/SSA 52 kDa proteins. The corresponding section of the remainder of the membrane was excised and incubated with patient serum for 30 minutes at 37° C. Following five TBST washes, bound antibodies were eluted using a modification of a method by Krohne, G., R. Stick, J. A. Kleinschmidt, R. Moll, W. W. Frankie, and P. Hausen *J. Cell. Biol.* 94:749–754 (1982). The membrane was incubated with patient serum for 30 minutes at 37° C., and the bound antibodies were eluted with 3 M sodium, rather than potassium, thiocyanate. The elution process was repeated five times and the resulting solution was concentrated approximately 50-fold using a Centriprep 30 concentrator (Amicon Division, W. R. Grace, Danvers, Mass.). Antibodies which bound to proteins produced in IPTG-induced plaque purified bacteriophage clones FI18.1 or FI19.3, or in wild type lambda gt11 as a control, were eluted in an identical manner from nitrocellulose blots.

Affinity purified antibodies isolated from Western blots of human lymphocyte or HeLa cell extracts were tested for their ability to bind to IPTG-induced proteins in clones FI18.1 and FI19.3, and in wild type lambda gt11 transfected E. coli cells. Affinity purified antibodies isolated from IPTG-induced proteins of these bacteriophage clones were used to determine their binding specificity to Western blots of human lymphocyte extracts using the method of Towbin, et al. (1979). The use of affinity purified antibodies in such assays was identical to that described for patient serum above, except that the affinity purified antibodies were used undiluted. Antibodies eluted from proteins from IPTG-induced clones FI18.1 and FI19.3, but not IPTG-induced lambda gt11 transfected *E. coli* cells, bound only to a 52 kDa protein in Western blots. Affinity purified antibody from the 52 kDa region of Western blotted lymphocyte extracts bound to IPTG-induced proteins of clones FI18.1 and FI19.3, and not IPTG-induced proteins of lambda gt11 transfected *E. coli*.

Immunoprecipitations of Ro/SSA Proteins and hY RNAs:

Affinity purified antibodies isolated from IPTG-induced proteins of clone FI18.1 or FI19.3 were used to immunoprecipitate nucleic acids from HeLa cells which are bound to Ro/SSA proteins using the technique of Forman, M. S., M. Nakamura, T. Mimori, C. Gelpi, and J. A. Hardin *Arthritis Rheum.* 28:1356–1361 (1985). These antibodies were bound to Staphylococcal protein-A-coated Sepharose™ CL-4B beads (Pharmacia, Piscataway, N.J.). HeLa cells were lysed by sonication in the presence of 0.05% Nonidet™-P40 (Non-phenyl-polyethylene glycol, a nonionic surfactant, also referred to as NP-40™) and mixed with these beads. Following washing of the beads, bound material was eluted with 0.3 M sodium acetate and 1% SDS, and subjected to phenol/chloroform extraction. Ethanol precipitated nucleic acids were dissolved in electrophoresis sample buffer and subjected to polyacrylamide gel electrophoresis in the presence of 7 M urea, and finally were silver stained. HY RNAs were identified using affinity purified antibodies from these clones, but not from IPTG-induced lambda gt11 transfected *E. coli*.

Characterization of DNA Inserts in Clones FI18.1 and FI19.3:

DNA was extracted from the bacteriophage clones, digested with the restriction enzyme EcoRI and electrophoresed in both agarose and polyacrylamide gels. Staining with ethidium bromide revealed that both clones contained a single 1.8 kilobase insert. DNA from each clone was subjected to electrophoresis in 0.8% agarose gels and transferred to nylon membranes (Amersham, Arlington Heights, Ill.) by the method of Southern, E. M. *J. Mol. Biol.* 98:503–517 (1978). Isolated inserts were radioactively labeled with α-$^{32}$P-dCTP using random hexamer primers by the procedures of Feinberg, A. P., and B. Vogelstein *Anal Biochem* 132:6–13 (1983) and Feinberg, A. P., and B. Vogelstein *Anal. Biochem.* 137:266–267 (1984), and hybridized to nylon membranes to analyze their sequence similarity in cross-hybridization studies. Following hybridization, the resulting membranes were washed under high stringency with 0.1×SSPE (15 mM NaCl, 1 mM NaH$_2$PO$_4$, 0.1 mM EDTA, pH 7.0) and 0.1% SDS at 65° C. Hybridization was detected by autoradiography. Cross-hybridization of inserts of clones FI18.1 and FI19.3 was detected.

The EcoRI inserts from each bacteriophage clone were purified following electrophoresis through preparative 5% N,N'-bis-acrylylcystamine cross-linked polyacrylamide gels (Bio-Rad Laboratories, Richmond, Calif.), reduction in 2-mercaptoethanol, and DEAE ion-exchange chromatography. The resulting fragments were subcloned into an EcoRI digested M13mp19 bacteriophage vector, as described by Yanisch-Perron, C., J. Vieira, and J. Messing *Gene* 33:103–119 (1985). Additional DNA from clone FI18.1 was digested with other restriction enzymes chosen for their ability to produce DNA fragments which could be directly subcloned into the multiple cloning sites of M13mp19. Following ligation of these inserts to the vectors with T4 DNA ligase (Bethesda Research Laboratories, Gaithersburg, Md.), DNA was transformed in *E. coli* strain JM103. Single stranded DNA from M13 subclones was prepared by the method of Sanger, F., S. Nicklen, and A. R. Coulsen *Proc. Natl. Acad. Sci. USA* 74:5463–5467 (1977), and subjected to nucleotide sequencing using the dideoxy chain-termination method of Sanger, F., A. R. Coulson, B. G. Barrell, A. J. H. Smith, and B. A. Roe *J. Mol. Biol.* 143:161–178 (1980) and T7 DNA polymerase, as reported by Tabor, S., and C. C. Richardson. *Proc. Natl. Acad. Sci. USA* 84:4767–4771 (1987) (U.S. Biochemical Corp., Cleveland, Ohio). Additional nucleotide sequence was determined from deletion subclones which were produced using the exonuclease activity of T4 DNA polymerase from M13 phage clones containing large inserts, using the technique of Dale, R. M. K., B. A. McClure, and J. P. Houchins *Plasmid* 13:31–40 (1985). The resulting nucleotide sequence of this cDNA molecule is shown in FIGS. 1A–1D. Computer analysis of nucleotide sequences were performed using the Sequence Analysis Software Package of the Genetics Computer Group, University of Wisconsin, described by Devereux, J., P. Haeberli, and O. Smithies *Nucl. Acids Res.* 12:387–395 (1984), and programs written for use on the IBM PC, including modification of those described by Schwindinger, W. F., and J. R. Warner *Nucl. Acids Res.* 12:601–604 (1984).

Methods for Expression of Large Quantities of Protein from the cDNA.

Methods for Production of Recombinant Proteins.

In Bacteria.

The protein can be expressed following IPTG induction from the lambda gt11 cDNA clone, or subclones of this cDNA in plasmids, or a portion thereof, or as modified using standard techniques, as described above.

In Human or Animals Cell Culture.

The protein can also be expressed from the cDNA, or a portion thereof, or as modified using standard techniques, following subcloning of the cDNA into a eukaryotic expression vector containing well characterized viral promoters and enhancers such as SV40 regulatory regions (Chu, G. and P. A. Sharp, *Gene* 13:197–202 (1981); the bovine papilloma virus (Howley, P. M., N. Sarver, and M. F. Law, *Methods Enzymol.* 101:357–402 (1983); or other expression vectors. These recombinant molecules can then be introduced into appropriate eukaryotic cells using the protoplast fusion technique (Schaffner, W., *Proc. Natl. Acad. Sci. USA* 77:2163–2167 (1986); Sadri-Goldin, R. M., et al., *Methods Enzymol.* 101:402–411 (1982)), CaPO$_4$ precipitation (Graham, F. L. and A. J. van der Eb *Virology* 52:456–457 (1973)), or other known methods. These recombinant molecules existing as either episomes, or as single or concatemeric copies integrated into chromosomal DNA can form stable transformed cells lines for expression of cDNA encoded proteins.

Following lysis of transfected bacterial or eukaryotic cells, the 52 kDa Ro/SSA protein can be purified with known methods including ion-exchange chromatography. Alternatively, the protein may be secreted from such cells depending on the host/vector system or modifications to the cDNA, and the resulting protein can be purified from cellular supernatants. The purity can be monitored by SDS-PAGE and immunodetection assays such as ELISA assays, radioimmunoassays, or Western blots.

Methods of Production of Antibodies to the Recombinant Proteins.

Polyclonal Antisera Produced by Immunization of Animals.

Animals can be immunized using standard techniques with the purified protein expressed from the cloned cDNA in order to produce polyclonal sera. Alternatively, monoclonal antibodies can be produced as follows, or using other methods also known to those skilled in the art.

Monoclonal Antibodies Produced by Hybridomas.

BALB/c mice are injected intraperitoneally with 50–100 µg of purified protein in complete Freund's adjuvant. The mice are again immunized after 3 weeks with the protein emulsified in incomplete Freund's adjuvant and after 6 weeks with the protein in TBS (0.1 M NaCl 0.02 M Tris-HCl pH 7.5). Four days later, spleen cells are fused with the mouse myeloma cell line P3X63AG8653 using 35% polyethylene glycol 1450, using standard techniques, as described by Laurell, M., K. Ikeda, S. Lindgren, J. Stenflo, *FEBS Letters* 191, 75–81 (1985); Wakabayashi, K., Y. Sakata, N. Aoki, *J. Biol. Chem.* 261, 11097–11105 (1986); Borrebaeck, C. A. K., M. E. Etzler, *J. Biol. Chem.* 256, 4723–4725 (1981); Kohler, G., C. Milstein, *Nature* 256, 495–497 (1975).

Cells are grown in HAT medium to select for hybridomas. After four weeks, supernatants from fused cells are screened for antibody production by solid-phase enzyme-linked immunoadsorbent assay in the presence and absence of 5 mM $Ca^{2+}$.

Positive clones of interest, as determined on the basis of reactivity with antigen, are recloned at least two times by limiting dilution onto murine peritoneal lavage feeder cells.

A BALB/c mouse is initially primed with pristane to induce ascites fluid production and, 14 days later, injected intraperitoneally with 0.1 ml of 10 mg/ml cyclophosphamide in order to immunocompromise the animal. Seventy-four hours later, $3-6 \times 10^6$ cells are injected intraperitoneally. After 7–10 days, ascites fluid is collected and monoclonal antibodies purified from ascites fluid. Antibody is normally present at 8–15 mg antibody/ml ascites fluid. Two different methods can be used to purify the antibody: (1) $NH_4SO_4$ fractionation followed by QAE-Sephadex chromatography; or (2) affinity chromatography on antigen bound Affi-Gel™ 10.

Alternatively, selected hybridomas can be propagated in vitro in laboratory culture vessels from which the monoclonal antibodies against the selected antigen can be harvested by decantation and purified as described for the ascites fluid. The antigen affinity resin can also be used to isolate the monoclonal antibodies from hybridoma tissue culture supernatants. The material is directly applied to the column. The antibody concentration in an exponentially growing culture is approximately 25 µg/ml.

Xenogeneic Antibodies Produced In Severe Combined Immunodeficient Mice.

Adult retired breeder mice C.B-17 SCID (homozygous for SCID mutation) are obtained from the Fox Chase Cancer Institute and bred and maintained in a sterile environment. At 24 weeks of age or older, mice are removed from the sterile environment and injected with human peripheral blood mononuclear cells, using the method of Mosier, D. E., R. J. Galizia, S. M. Baird, D. B Wilson *Nature* 335, 256–259 (1988). Mice are subsequently fed standard non-sterile mouse chow and kept in isolation laminar flow cubicles (BioClean, Inc.). SCID mice are bled by tail vein.

Human peripheral blood mononuclear cells are obtained from patients having autoantibodies. Approximately 150 ml of blood is withdrawn into a heparinized container (preservative-free) and mononuclear cells separated by low speed density centrifugation (Histopak, Sigma Chemical Co., St. Louis, Mo.). Viability is determined by exclusion of trypan blue. Various numbers ($\times 10^6$) of isolated human mononuclear cells are injected intraperitoneally.

Enzyme linked immunosorbent assays (ELISA), performed using established techniques, as described by Gaither and Harley, *Protides Biol. Fluids Proc. Collog.* 33, 413 (1985), are used to screen for the production of human IgG and specific autoantibodies. To screen for human IgG production, 96 well microtiter plates are coated with mouse serum at limiting dilutions. They are subsequently washed, blocked and goat anti-human IgG (gamma chain specific) alkaline phosphatase conjugate (Sigma Chemical Co., St. Louis, Mo.) added. After overnight incubation, microtiter plates are washed, substrate added and optical density readings taken on an ELISA reader (Beckman Instruments).

Engrafted mouse sera are screened for autoantibodies using a standard anti-Ro/SSA ELISA and highly purified Ro/SSA. Engrafted mouse sera is analyzed for anti-nuclear antibodies on Hep-2 cells using a NOVA Lite ANA (INOVA DIAGNOSTICS, Inc., San Diego, Calif.). Serum samples are diluted and 50–75 µl applied to each substrate slide. After 30 min incubation in a moist chamber at room temperature, the slides are thoroughly washed with PBS. Goat anti-human IgG gamma chain specific FITC conjugate (Sigma Chemical Co., St. Louis, Mo.) is added at 1:7500 dilution and incubated for 30 min at room temperature. Slides are subsequently washed with PBS and immunofluorescent staining visualized under a fluorescence microscope.

Modifications and variations of the cDNA and protein expressed therefrom, and methods for use thereof, will be obvious to those skilled in the art from the foregoing detailed description of the invention. Such modifications and variations are intended to come within the scope of the appended claims.

We claim:

1. An isolated nucleic acid molecule separate from the human genome encoding a Ro/SSA human autoantigen having a molecular weight by SDS-PAGE and Western blot of 52 kDa, or encoding an effective amount of the amino acid sequence of the Ro/SSA autoantigen to form an epitope immunoreactive with an anti-Ro/SSA autoantibody and which is isolated by a process comprising hybridizing under standard conditions to nucleic acid probes having the sequence set forth in FIG. 1 or portions thereof.

2. The molecule of claim 1 consisting essentially of a protein encoding fragment, wherein the protein encoding fragment is a fragment between nucleotide position number 39 and nucleotide position number 1466 of the sequence set forth in FIG. 1.

3. The molecule of claim 1 comprising the entire sequence set forth in FIG. 1.

4. The molecule of claim 1 labelled with a detectable label for use as a probe.

5. An isolated nucleic acid molecule separate from the human genome consisting of nucleotides 1 to 38 of the sequence set forth in FIG. 1.

6. An isolated nucleic acid molecule separate from the human genome consisting of nucleotides 1467 to 1843 of the sequence set forth in FIG. 1.

7. The nucleic acid molecule of claim 1 further comprising expression vector sequences for expression in prokaryotes or eukaryotes.

* * * * *